US00PP19256P2

(12) United States Plant Patent
Pierce

(10) Patent No.: US PP19,256 P2
(45) Date of Patent: Sep. 23, 2008

(54) ***CALIBRACHOA* PLANT NAMED 'CAL PAICORAS'**

(50) Latin Name: ***Calibrachoa* sp.**
Varietal Denomination: Cal Paicoras

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/881,852

(22) Filed: Jul. 30, 2007

(51) Int. Cl.
*A01H 5/00* (2006.01)

(52) U.S. Cl. ..... Plt./413
(58) Field of Classification Search ..... Plt./413
See application file for complete search history.

*Primary Examiner*—Kent L. Bell
*Assistant Examiner*—June Hwu
(74) *Attorney, Agent, or Firm*—Jondle & Associates, P.C.

(57) ABSTRACT

A new *Calibrachoa* plant particularly distinguished by coral flowers with light pink margins and darker red mid-veins, early and continuous flowering, narrow, dark green foliage, good vigor, semi-upright to later prostrate or trailing plant habit, is disclosed.

1 Drawing Sheet

Genus and species: *Calibrachoa* sp.
Variety denomination: 'Cal Paicoras'.

BACKGROUND OF THE NEW PLANT

The present invention comprises a new and distinct cultivar of *Calibrachoa,* botanically known as *Calibrachoa* sp., and hereinafter referred to by the cultivar name 'Cal Paicoras'. The new cultivar originated from a hybridization made in July 2003 in Gilroy, Calif. The female parent was the red-purple with cream margins-flowered *Calibrachoa* plant 'Cal Rostar' (U.S. Plant Pat. No. 16,772), while the male parent was the scarlet-flowered *Calibracho* plant 'Cal Scaredtwo' (U.S. Plant Pat. No. 16,771). The seeds produced by the hybridization were sown in January 2004 in Gilroy, Calif. A single plant selection was chosen for further evaluation and for asexual propagation in April 2004 in Gilroy, Calif.

The new cultivar was created in 2003 in Gilroy, Calif. and has been asexually reproduced repeatedly by vegetative cuttings and tissue culture in Gilroy, Calif. Andijk, The Netherlands and Hillscheid, Germany over a three-year period. The plant has also been trialed at Gilroy, Calif. Andijk, The Netherlands and Hillscheid, Germany. The present invention has been found to retain its distinctive characteristics through successive asexual propagations.

Plant Breeder's Rights for this cultivar were applied for in the European Union on Feb. 26, 2007 and in Switzerland on Oct. 30, 2006.

SUMMARY OF THE INVENTION

The following are the most outstanding and distinguishing characteristics of this new cultivar when grown under normal horticultural practices in Gilroy, Calif. and Hillscheid, Germany.

1. Coral flowers with light pink margins and dark red mid-veins;
2. Narrow, dark green foliage;
3. Good vigor;

4. Semi-upright to later prostrate to trailing plant habit; and
5. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of whole plants about 20-weeks old, grown in a greenhouse in Hillscheid, Germany. The potted plant photograph was taken in May. The basket plants were moved outside to grow in the summer and the photograph was taken in August.

DESCRIPTION OF THE NEW CULTIVAR

Figure 1:
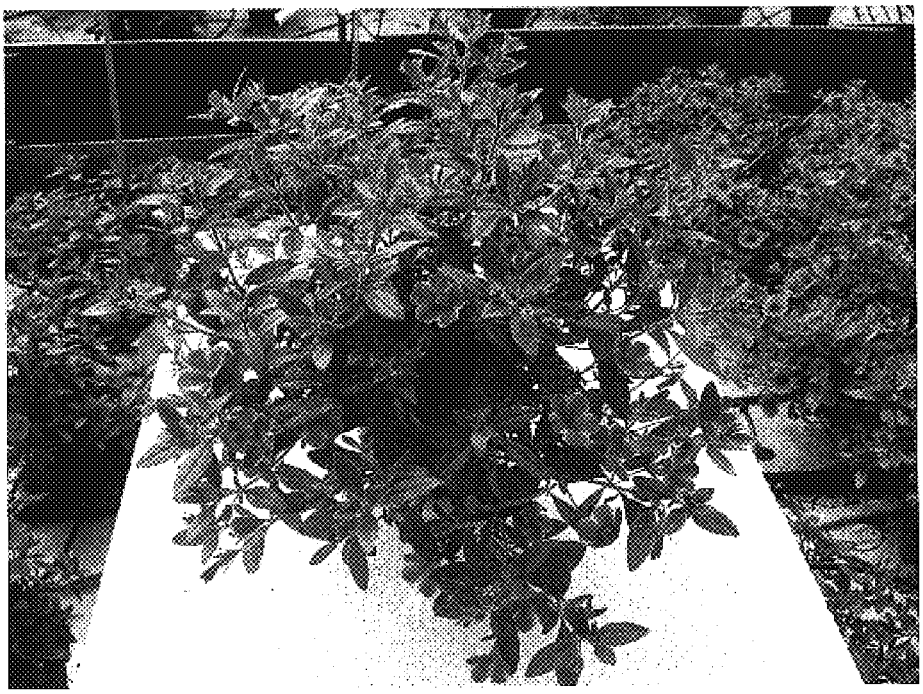
FIG. 1 shows a close-up of the mature flowers.
Figure 2:
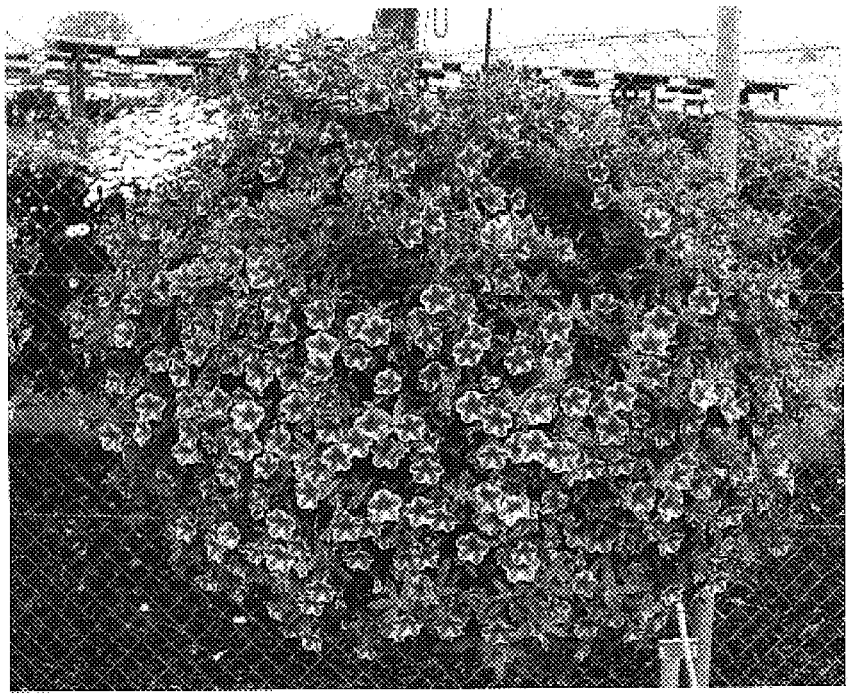
FIG. 2 shows the overall plant habit, including blooms, buds, and foliage.

The following detailed description sets forth the distinctive characteristics of 'Cal Paircoras'. The data which define these characteristics were collected from asexual reproductions carried out in Gilroy, Calif. The plant history was taken on 16-week old plants grown in 6-inch pots in a greenhouse in the spring season in a trial setting. The plants had one plant growth regulator treatment and one terminal pinch after cuttings were transplanted to the 6-inch pots. Color readings were taken under natural light in the greenhouse. Color references are primarily to the R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:

*Female parent.*—'Cal Rostar', a red-purple with cream margins-flowered *Calibrachoa* plant (U.S. Plant Pat. No. 16,772).

*Male parent.*—'Cal Scaredtwo', a scarlet-flowered *Calibrachoa* plant (U.S. Plant Pat. No. 16,771).

Growth:

*Form.*—Semi-upright and decumbent (initially spreading to later prostrate and trailing).

*Habit.*—Good vigorous habit, well-branched, full plant; early and continuous flowering response.

*Height* (*measured from the top of the soil*).—8.0 cm to 12.0 cm.

*Width* (*horizontal plant diameter*).—45.0 cm to 55.0 cm.

*Time to produce a finished flowering plant.*—10 weeks.

*Outdoor plant performance.*—Full sun; used as a hanging plant, in mixed container plantings, mass planting in a bed.

*Time to initiate and develop roots.*—18 to 23 days.

*Root description.*—White, fibrous.

Stems:

*Length of basal branches.*—24.0 cm to 26.0 cm.

*Internode length.*—0.5 cm to 1.0 cm.

*Diameter of branches* (*from midpoint*).—0.15 cm.

*Stem color.*—RHS 144B.

*Texture.*—Glandular hairs of various sizes.

*Anthocyanin.*—Absent.

*Pedicel color.*—RHS 144A.

*Pedicel length.*—1.5 cm to 2.7 cm.

*Pedicel diameter.*—0.1 cm.

*Pedicel texture.*—Glandular hairs of various sizes.

Leaves:

*Arrangement.*—Alternate; upper leaves sub-opposite.

*Size.*—Length: 2.0 cm to 2.1 cm. Width: 0.7 cm to 0.8 cm.

*Shape.*—Elliptical.

*Margin.*—Entire.

*Apex.*—Slightly rounded to obtuse.

*Base.*—Acuminate.

*Color.*—Immature: Upper surface: RHS 137B to RHS 137C. Lower surface: RHS 137C. Mature: Upper surface: RHS 137A. Lower surface: RHS 143B.

*Texture.*—Glandular hairs.

*Venation.*—Pinnate.

*Venation color.*—RHS 144B, mainly at midrib, otherwise indistinct.

*Petioles.*—Length: 0.15 cm to 0.2 cm. Width: 0.1 cm. Color: RHS 144B. Texture: Many glandular hairs of various sizes.

Flower bud:

*Shape.*—Oblong.

*Size.*—Length: 1.5 cm to 2.0 cm. Diameter: 0.4 cm to 0.5 cm.

*Color at tight bud.*—RHS 39B.

Inflorescence:

*Blooming habit.*—Continuous throughout the growing season; good floriferousness.

*Inflorescence type.*—Flowers solitary in upper leaf axis.

*Floret type.*—Funnel form; 5 lobed petals, fused at base.

*Lastingness of individual blooms on the plant.*—5 to 8 days.

*Fragrance.*—Absent.

Flowers:

*Immature flower.*—Diameter: Hortizontal: 2.2 cm to 2.5 cm. Vertical: 2.2 cm to 2.4 cm. Color: Upper surface: RHS 53B to RHS 53C; RHS 53B at the corolla opening; RHS 38C to RHS 38D margins; RHS 59A mid-vein; RHS 53C veins. Lower surface: RHS 54D; some petals have a little RHS 54B on one half of the petal; RHS 24D margins; RHS N77A mid-veins; RHS N77D veins.

*Mature flower: Diameter: Horizontal:* 2.7 cm to 2.9 cm. Vertical: 2.8 cm to 3.0 cm. Color: Upper surface: RHS 53C to RHS 53D; RHS 53B at the corolla opening; RHS 38C to RHS 38D margins; RHS 59A mid-veins; RHS 53C veins; Lower surface: RHS 54D; some petals have a little RHS 54B on one half of the petal; RHS 24D margins; RHS N77A mid-veins; RHS N77D veins.

*Corolla tube.*—Color inside: RHS 9A; RHS N200B veins. Color outside: RHS 5C; RHS N77A mid-veins; RHS N77C veins. Tube length: 1.5 cm to 1.7 cm. Outside texture: Glandular hairs of various sizes.

*Petals.*—Apex: Mucronulate. Base: Fused. Margin: Entire. Waviness of petals: Very weak. Lobation: Moderate. Texture: Papillose.

*Sepals.*—Calyx: 5 sepals fused at base and somewhat outwardly reflexed. Shape: Lanceolate. Apex: Acute. Base: Fused. Margin: Entire. Length: 1.1 cm to 1.3 cm. Width: 0.2 cm. Color: Upper surface: Slightly darker than RHS 144A. Lower surface: RHS 144A. Texture: Glandular hairs of various sizes.

Reproductive organs:

*Stamens.*—Number: 5; 2 long, 3 short. Filament color: RHS 3D. Filament length: 0.7 cm to 1.0 cm. Filament diameter: Less than 0.1 cm. Pollen color: RHS 3B. Pollen quantity: Moderate.

*Pistils.*—Number: 1. Length: 1.1 cm. Diameter: Less than 0.1 cm. Stigma color: RHS N144A. Style color: RHS 3D.

Fruit and seed set: No seed set observed.

Disease and insect resistance: No particular resistance or susceptibility has been observed.

COMPARISON WITH PARENTAL/ COMMERCIAL CULTIVARS

'Cal Paicoras' differs from the female parent 'Cal Rostar' (U.S. Plant Pat. No. 16,772) by having larger flowers that are more coral in color than the rose colored flowers of 'Cal Rostar'. 'Cal Paicoras' shorter, green leaves than 'Cal Rostar'. Additionally, 'Cal Paicoras' is more floriferous and has a taller plant height than 'Cal Rostar'.

'Cal Paicoras' differs from the male parent 'Cal Scaredtwo' (U.S. Plant Pat. No. 16,771) by having smaller leaves and a more prostrate growth habit than 'Cal Scaredtwo'. Additionally, 'Cal Paicoras' is earlier to flower than 'Cal Scaredtwo'.

'Cal Paicoras' differs from the commercial comparison variety 'Balcabhopi' (U.S. Plant Pat. No. 18,795) in that 'Cal Paicoras' has coral-colored flowers with light-pink margins and dark red mid-veins, while 'Balcabhopi' had dark-ink-colored flowers with greyed-purple venation.

I claim:

1. A new and distinct cultivar of *Calibrachoa* plant as shown and described herein.

* * * * *